United States Patent

Mottola et al.

[11] Patent Number: 5,957,901
[45] Date of Patent: Sep. 28, 1999

[54] CATHETER WITH IMPROVED SPRAY PATTERN FOR PHARMACO-MECHANICAL THROMBOLYSIS THERAPY

[75] Inventors: Jim Mottola, South Jordan; Steve W. Carlstrom, Salt Lake City; Andy E. Poursaid, Sandy, all of Utah

[73] Assignee: Merit Medical Systems, Inc., South Jordan, Utah

[21] Appl. No.: 08/949,893

[22] Filed: Oct. 14, 1997

[51] Int. Cl.⁶ .............................. A61M 5/00; A61M 25/00
[52] U.S. Cl. ........................ 604/264; 604/269; 604/508
[58] Field of Search ................... 604/29, 30, 53, 604/54, 55, 93, 118, 121, 280, 912, 264, 272, 271; D24/112; 138/111

[56] References Cited

U.S. PATENT DOCUMENTS

| | | | |
|---|---|---|---|
| 4,256,102 | 3/1981 | Monaco | 128/213 |
| 4,491,126 | 1/1985 | Cullor | 604/55 |
| 4,927,418 | 5/1990 | Dake et al. | 604/264 |
| 4,968,307 | 11/1990 | Dake et al. | 604/164 |
| 5,052,998 | 10/1991 | Zimmon | 604/281 |
| 5,069,673 | 12/1991 | Shwab | 604/280 |
| 5,098,413 | 3/1992 | Trudell et al. | 604/280 |
| 5,141,499 | 8/1992 | Zappacosta | 604/280 |
| 5,156,597 | 10/1992 | Verreet et al. | 604/280 |
| 5,250,034 | 10/1993 | Appling et al. | 204/164 |
| 5,389,074 | 2/1995 | Parker et al. | 604/96 |
| 5,480,392 | 1/1996 | Mous | 604/280 |
| 5,569,197 | 10/1996 | Helmus et al. | 604/96 |
| 5,713,861 | 2/1998 | Vanarthos | 604/53 |
| 5,738,649 | 4/1998 | Macoviak | 604/53 |
| 5,800,407 | 9/1998 | Eldor | 604/264 |

OTHER PUBLICATIONS

McNamara, Thomas O., Role of Thrombolysis in Peripheral Arterial Occlusion, *the American Journal of Medicine*, vol. 83:6–10, Aug. 24, 1987.

*Primary Examiner*—Wynn Wood Coggins
*Assistant Examiner*—Sharon Finkel
*Attorney, Agent, or Firm*—Workman, Nydegger, Seeley

[57] ABSTRACT

An improved catheter includes a double spiral configuration of infusion holes around the circumference and along the length of the catheter which provides an improved lateral dispersion of a thrombolytic fluid to more completely and quickly lyse a clot through which the catheter is passing. The double spiral configuration consists of groups or sets of infusion holes, typically groups of four. The holes in each set are longitudinally spaced from each other at substantially regular intervals along the length of the catheter. Each successive hole in a given group is circumferentially spaced by an angular distance of about 90° around the circumference of the catheter relative to the immediately preceding hole. Each group of holes is circumferentially spaced or offset by an angular distance of between 1° and 89° relative to the immediately preceding group of holes. Typically, the angular spacing between successive groups of holes is 18°.

20 Claims, 5 Drawing Sheets

CATHETER WITH IMPROVED SPRAY PATTERN FOR PHARMACO-MECHANICAL THROMBOLYSIS THERAPY

BACKGROUND OF THE INVENTION

1. The Field of the Invention

The present invention relates to specialized catheters used in the treatment of thromboembolic occlusions in a patient's circulatory system. More specifically, the present invention relates to improved catheters which deliver thrombolytic fluids to the site of a thrombus or blood clot and which provides an improved lateral dispersion, or spray pattern, of the thrombolytic fluid.

2. The Relevant Technology

A reasonably common and dangerous medical condition arises when a blood clot develops in a patient's circulatory system. A blood clot or thrombus can endanger the health of a patient in at least two significant ways. First, the clot may restrict or even completely stop essential blood flow to a portion of the patient's body. If the blood flow to the brain or heart for example is restricted the patient's life may be placed in jeopardy. Additionally, a clot may break loose from the site at which it formed and be carried by the blood stream to an organ, such as the heart, where it may cause irreparable damage or even death. Accordingly, when a blood clot is detected, it must be quickly and effectively treated.

One method involves surgery to remove the clot and repair the blood vessel, another method mechanically breaks up an existing clot into smaller micro-emboli. A less invasive method uses thrombolytic drugs to break up, or lyse, the thrombus. This method of treating a blood clot consists of inserting a catheter into the patient's circulatory system, preferably near the site of the clot. If the catheter enters the circulatory system near the clot, the catheter alone may be used. If, for a variety of reasons, the catheter must be inserted into the circulatory system at a distance from the clot, placement of the catheter may be aided by using a guide wire or introducer sheath, which can be used to push and guide the catheter through the vessels or arteries of the circulatory system to reach the clot.

Once the catheter is positioned at the site of the clot, a thrombolytic fluid capable of dissolving the clot, such as urokinase or streptokinase, is delivered to the site of the clot by means of the catheter. Conventional catheters have a lumen, i.e., an internal passage, that allows the thrombolytic fluid to flow through the catheter to one or more discharge openings, or sideholes, at or near the distal end of the catheter. The discharged thrombolytic fluid then dissolves or lyses the clot, thus removing the danger to the patient.

Not all clots are easily or successfully lysed. Some clots form around arterial lesions, which clots may not be easily lysed or broken up by the thrombolytic fluid and which usually require surgical removal. Additionally, some clots may be extremely thick, extending for a relatively long distance through a blood vessel of the circulatory system. Such a thick clot may require considerable amounts of time and heavy irrigation of thrombolytic fluid to dissolve.

Typically, a guidewire is used in conjunction with a catheter to facilitate placement of the catheter. The guidewire can also serve to penetrate the clot in order to form a passage therethrough so that the catheter can be inserted within the interior of the clot. This helps to ensure that the thrombolytic fluid is concentrated or focused at the location of the clot, since excessive thrombolytic fluid in the bloodstream can have adverse effects on the patient.

After the guide wire has been used to create a narrow passage through the clot, particularly a thick clot, the thrombolytic fluid is released through the one or more openings within the catheter. In the beginning stages of thrombolytic therapy, thrombolysis was carried out using a catheter with a single opening at the distal end of the catheter. McNamara, T., "Role of Thrombolysis in Peripheral Arterial Occlusion," *Am. J. Med.*, Vol. 83 (Suppl. 2A), pp. 6–10, Aug. 24, 1987. Methods employing a simple catheter required movement of the catheter from one end of the clot to the other while dispensing the thrombolytic fluid in order to adequately distribute the fluid over the entire length of the thrombus.

Subsequent improvements have been made in an attempt to create a more uniform distribution of thrombolytic fluids along the length of the blood clot. A catheter having slits or other pressure activated one-way openings arranged radially at 90° intervals around the circumference of the catheter and in sets of four longitudinally spaced intervals along the length of the catheter is disclosed in U.S. Pat. No. 5,250,034 to Appling et al. A hollow infusion guidewire having sets of four holes, each hole radially separated by 90° intervals around the circumference of the guidewire and each set of four holes spaced longitudinally along the length of the guidewire is set forth in U.S. Pat. No. 5,569,197 to Helmus et al. Catheters having holes individually spaced at regular intervals along the length of the catheter and spaced radially at 90° intervals relative to each previous hole are set forth in U.S. Pat. Nos. 4,968,307 and 4,927,418 to Dake et al.

Whether the infusion holes are grouped together in sets of four holes spaced at 90° intervals around the catheter or staggered to form a spiral configuration with individually staggered holes spaced at 90° intervals, the result is the same: infusion holes that are arranged along four parallel lines radially spaced at 90° intervals around the catheter wall.

Although such hole patterns are superior to a simple catheter having a single hole at the distal end, they are only able to distribute thrombolytic fluids at discrete 90° intervals around the circumference of the catheter. The area between the 90° intervals does not receive as much thrombolytic fluid, thus resulting in a poor overall distribution of thrombolytic fluid.

Accordingly, there exists a need in the art for improved catheters which can more completely and evenly disperse thrombolytic fluid around the circumference of a catheter in order to more effectively and efficiently lyse blood clots in a patient's blood vessel. There also exists a need for improved catheters which ensure a more consistent dispersion rate between catheters of different infusion lengths.

SUMMARY AND OBJECTS OF THE INVENTION

Accordingly, it is an object of the present invention to meet the above-described need in the art for an improved catheter. It is an object of the present invention to provide an improved catheter which is capable of more completely and evenly dispersing a thrombolytic fluid around the lateral circumference of the catheter to more quickly and completely lyse a thrombus through which the catheter has been passed. It is also an object to provide catheters that ensure a more consistent fluid dispersion rate between catheters of different infusion lengths.

These and other objects and features of the present invention will become more fully apparent from the following description and appended claims, or may be learned by the practice of the invention as set forth hereinafter.

The catheter of the present invention includes a main lumen through which a thrombolytic fluid can be delivered. The open distal end of the catheter is occluded using, e.g., a ball wire that has a diameter greater than the inner diameter of the distal end of the catheter. Anywhere along the usable length of the catheter, preferably near the distal end of the catheter, is a section, referred to as the infusion length, that includes infusion holes that are preferably arranged in a double spiral configuration. The infusion holes allow for passage of thrombolytic fluid from the central lumen to the blood clot being treated. The double spiral configuration creates a more complete dispersion of thrombolytic fluids.

The individual infusion holes are preferably spaced along the length of the catheter at regular intervals; for example, at longitudinal intervals of 0.05 inch. The infusion holes are grouped together in sets of holes, typically four holes, which are radially spaced apart at 90° intervals from each preceding hole within the same set. Each successive set of holes is preferably rotated relative to the immediately preceding set of holes by about 18° in order to create a staggered hole arrangement that results in a more diverse spray pattern. Although each set of holes is staggered relative to an immediately preceding set of holes by about 18°, the holes within successive sets of holes will nevertheless be incrementally and circumferentially spaced apart in 90° intervals as in the first set.

Thus, in a preferred embodiment, the second infusion hole will be circumferentially spaced at an interval of 90° relative to the first infusion hole, the third infusion hole will be circumferentially spaced 180° with respect to the first infusion hole, while the fourth infusion hole will be circumferentially spaced 270° with respect to the first infusion hole. However, rather than being spaced at 360° (or 0°) relative to the first hole, the fifth infusion hole will begin a new group of four holes and will be circumferentially spaced from the first infusion hole by some amount between 1° and 89°, most preferably about 18°, since this value divides evenly into the 360° (and 90°) so that a very regular yet well spaced arrangement of holes can be attained.

Thereafter, the sixth, seventh and eighth holes will be circumferentially spaced at successive 90° intervals relative to each other just like in the first set of holes. The ninth hole will preferably begin the third set of four holes and will be offset from the fifth hole by, e.g., about 18° and the first hole by about 36°. This pattern repeats itself substantially regularly along the entire infusion length of the catheter. Other angles that divide evenly into 360°, but not necessarily 90° or 180° may also be used depending on the desired spray pattern. In addition, angles that do not divide evenly into 360° may be used in order to yield an even more randomized spray pattern. However, fluid dynamics may dictate that the circumferential distance, or angle, of offset be within a certain range in order to ensure substantially even distribution of fluid through each of the holes along the infusion length.

While the usable catheter length may vary between about 45 to about 135 cm., the infusion length will vary between about 5 to about 50 cm., with generally diminishing hole size as the number of holes is increased in order to maintain substantially even fluid flow through the holes. In general, the catheter will be a 5 French catheter having an outer diameter of 0.068"±0.0015" and an inner diameter of 0.048"±0.0015". Of course, 4 and 3 French catheters may also be used depending on the application.

The hole size will generally range between about 0.002"–0.006", with the hole size generally decreasing as the number of holes is increased. Nevertheless, the size of catheter and infusion hole can be altered, as can be the longitudinal spacing between the holes, depending on the intended use of the catheter. Radiopaque marker bands are preferably employed to bracket the infusion length in order to provide the user with means for positioning the infusion length at a desired location within the blood vessel.

The double spiral configuration of the present invention provides a significantly improved radial dispersion of thrombolytic fluid around the circumference of the catheter. The result is a more quickly and completely lysed blood clot using a reduced amount of thrombolytic fluid, which greatly contributes to the recovery and well-being of the patient.

Although it may be preferred for the holes to be arranged in sets of four holes, with each successive hole being circumferentially spaced from an immediately preceding hole by 90°, other arrangements are possible. Although the holes within a given set may be separated by a variety of different angles θ, it will be preferable that the number and spacing of the holes within a given set be such that they will complete a cycle of about 360° before beginning the next set of holes. Thus, if the set includes n holes, then the circumferential spacing between successive holes in a given set will preferably be 360°/n. Thus, in the preferred embodiment, each set of holes will include 4 holes, and the circumferential spacing will be 90° between successive holes within the set.

Moreover, although the angle of offset between successive sets of holes is most preferably 18°, any angle that yields a reasonably diverse spray pattern can be used. However, the offset angle δ will preferably divide evenly into 360°, more preferably δ will divide evenly into 18°, and most preferably δ will divide evenly into 90°. Selecting δ so that it divides evenly into 360°, 180° or 90°, respectively, ensures some regularity of the hole pattern such that it is not overly random.

There are other features that can aid the ability of the improved catheters of the present invention to perform their function of providing better delivery of thrombolytic fluids. Gradient hole sizes within the infusion length can be used to ensure a more even distribution of fluid, wherein the most proximal hole is the smallest where pressure is the greatest and the most distal hole is the largest where pressure is the smallest. As stated above, hole size is generally inversely proportional to the number of holes within the infusion length.

In order to use increased pressures, the fluid source may be connected to the infusion catheter using a luer connector with an increased thread length in order to prevent disconnections within the system. In addition, the occluding wire used to seal the end of the infusion catheter during use is typically narrower in diameter to facilitate flow through the catheter and spray distribution through the holes.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawing depict only a typical embodiment of the invention and are not therefore to be considered to be limiting of its scope, the invention will be described and explained with additional specificity and detail through the use of the accompanying drawings in which.

Figure 1:
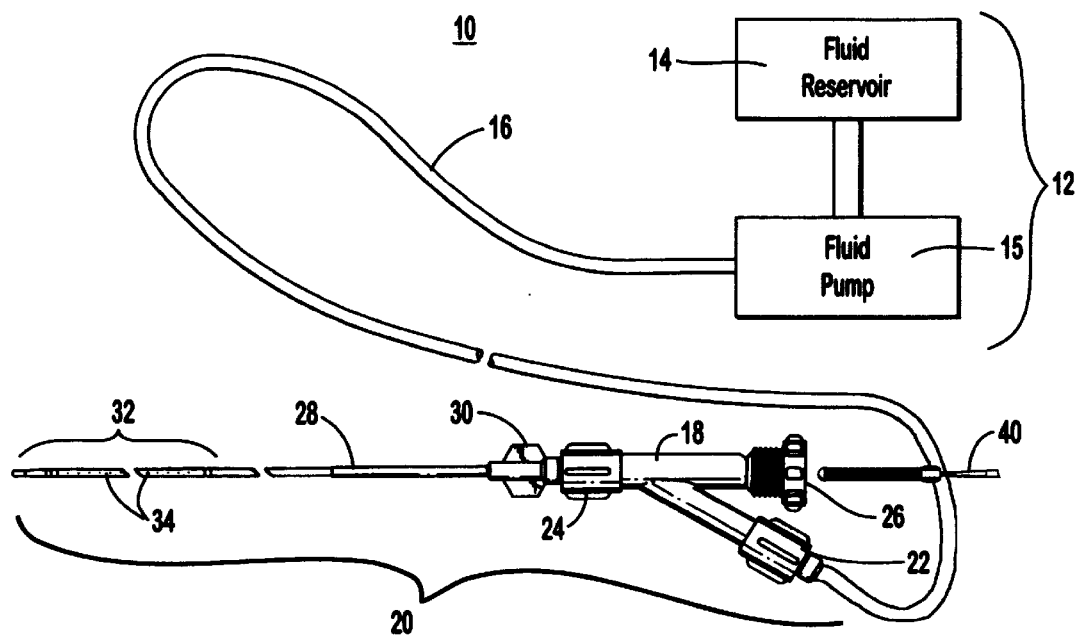
FIG. 1 is a side view of a generalized fluid delivery system used in conjunction with the improved catheters of the present invention.

DETAILED DESCRIPTION OF THE PREFERRED EMBODIMENTS

The present invention relates to improved infusion catheters used to irrigate selected portions of a person's body, particularly blood vessels occluded by a thrombus or blood clot. The catheters of the present invention have holes arranged in such a manner that a more disperse spray pattern is achieved, which results in the ability to more evenly spread the thrombolytic fluids throughout the blood clot. The inventive hole pattern is referred to as a "double spiral configuration," which is a vast improvement over typical spiral configurations in which successive holes within a group are circumferentially spaced apart at 90° intervals along the entire infusion length of the catheter. The double spiral configuration results in a more quickly and completely lysed blood clot using a reduced amount of thrombolytic fluid, which reduces harm to the patient that could result from the infusion of excessive thrombolytic agents.

The preferred thrombolytic agents used according to the present invention include any agent that can be used to lyse or break up a blood clot. Examples of preferred thrombolytic fluids include urokinase, streptokinase, and tissue plasminogen activator (TPA).

In order to illustrate the benefits of the catheters according to the present invention, reference is now made to the drawings. FIG. 1 depicts a generalized fluid delivery system that may be used in conjunction with the improved catheters of the present invention. As shown in FIG. 1, a fluid delivery system 10 comprises two subsystems, a fluid source system generally depicted as element 12 and a fluid infusion system generally depicted as element 20. The fluid source system 12 includes a fluid reservoir 14 in communication with a fluid pump 15, which in turn communicates with a fluid delivery tube 16, which is in turn connected to a three-way connector 18. The three-way connector 18 connects together the fluid source system 12 and the fluid infusion system 20. The three-way connector 18 includes a first end 22, a second end 24 and an occluding wire port 26. The fluid delivery tube 16 is connected to the first end 22.

The fluid infusion system 20 includes a single lumen catheter 28 that is attached to the second end 24 by means of a connector 30. The usable length of catheter 28 may vary between about 45 to about 135 cm. Near the distal end of the catheter 28 is an infusion length 32 that includes systematically placed infusion holes 34, which are spaced in an approximate double spiral configuration. Alternatively, the infusion length may be situated anywhere along the usable length of the catheter. The infusion length also preferably includes radiopaque marker bands (not shown) to assist in placing the infusion length in the proper location within the blood vessel.

The infusion holes are longitudinally spaced apart at substantially regular intervals along the length of the infusion length 32 of the catheter 28. In a preferred embodiment, the holes are grouped together in sets of four holes, with successive sets being circumferentially offset by an angular distance of, e.g., about 18°, relative to immediately preceding sets.

In a preferred arrangement depicted in FIG. 2, the holes 34 are arranged in a configuration such that each of the first set of four holes are incrementally spaced apart by a circumferential distance of about 90° in addition to being longitudinally spaced at substantially regular intervals of, e.g., 0.050". The next set of four holes is circumferentially offset by about 18°, relative to the first set of four holes. However, as in the first set, each successive hole in the second set is circumferentially offset from the immediately preceding hole by a circumferential distance of about 90° and longitudinally spaced at intervals of about 0.050".

Due to their being offset by an angular distance of about 18° relative to the first set, the four holes of the second set will not line up with the first set of four holes. Thus, the first hole of the second set of holes, which is the fifth hole, is rotated about 18° relative to the first hole of the first set. Likewise, the sixth hole is rotated about 18° relative to the second hole, the seventh hole is rotated about 18° relative to the third hole, and the eighth hole is rotated about 18° relative to the fourth hole.

The third set of four holes is likewise offset by a circumferential distance of about 18° relative to the second set of four hole, such that they are circumferentially offset by about 36° relative to the first set of holes. Thus, the ninth infusion hole is offset by 36° relative to the first hole and 18° relative to the fifth hole and so on. This pattern repeats itself such that each successive group of four holes is oriented an additional 18° relative to the previous set of four holes. Because it takes five sets offset by 18° to complete a cycle of 90°, it is not until the sixth set of holes that the holes are aligned at the same angular orientation as the holes of the first group. This creates a double spiral configuration that results in a more diversified spray pattern compared to where all the holes line up at 90° intervals, which occurs where there is no staggering, as in the prior art. This allows for much more evenly defused liquid through the infusion length 32.

In practice, the infusion catheter 28 is first inserted as desired into a desired location within a patient's artery or vein in order to infuse a liquid therein. The infusion catheter 28 can simply be inserted by itself or its insertion may be assisted by an introducer sheath (not shown) or a guidewire (not shown). An opening 36 at the distal end of the catheter 28 allows free passage of the guidewire therethrough to assist in placement of the catheter 28. Once the catheter 28 has been properly placed, the guidewire or introducer sheath can be removed from the patient. Thereafter, the catheter 28 can be connected to the three-way port 18 to provide fluid communication between the fluid source system 12 and the catheter 28.

The opening 36 at the distal end of the catheter must be occluded prior to irrigating a liquid through the infusion length 32. This may be accomplished by inserting an occluding ball wire 38 (FIG. 3) through the occluding wire port 26 of the three-way port 18. The occluding ball wire 38 includes a wire portion 40 and a sealing ball portion 42. Nevertheless, any occluding means known in the art may be used to seal the opening 36. However, it is preferable to use an occluding ball wire having a more narrow diameter to improve flow through the catheter 28 and improve the distribution pattern through holes 34.

Figure 3:
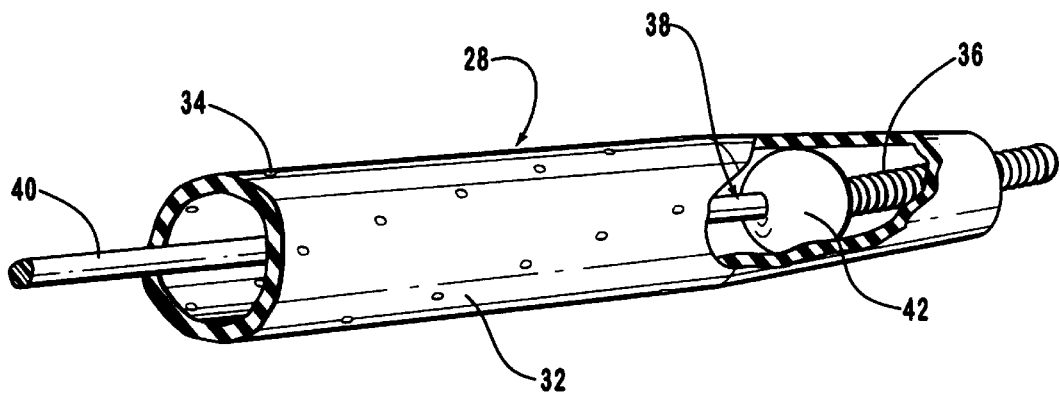
FIG. 3 is a breakaway perspective view of a portion of an inventive infusion catheter in combination with an occluding ball wire.

As depicted in FIG. 3, the occluding ball wire 38, when inserted substantially all the way through the catheter 28 and beyond the infusion length 32, is able to form a liquid-tight seal at the distal end of the catheter 28. Because the inner diameter of the catheter 28 is significantly larger than the diameter of the wire portion 40 of the occluding ball wire 38, there is ample space within the infusion catheter 28 for the passage of a liquid therethrough towards the infusion end 32. The inner diameter of the catheter 28 is reduced at the distal end such that the sealing ball portion 42 of the occluding ball wire 38 is able to seat against the inner wall of the catheter 28 and thereby effectively seal the opening 36. Thus, any liquid forced through the catheter 28 is caused to exit through the infusion hole 34 rather than the opening 36.

Figure 2:
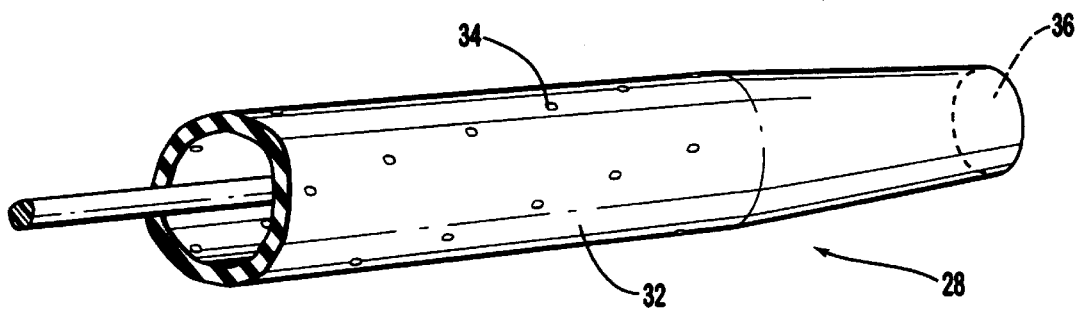
FIG. 2 is a breakaway perspective view of a portion of the infusion length of an infusion catheter according to the present invention.
Figure 4:
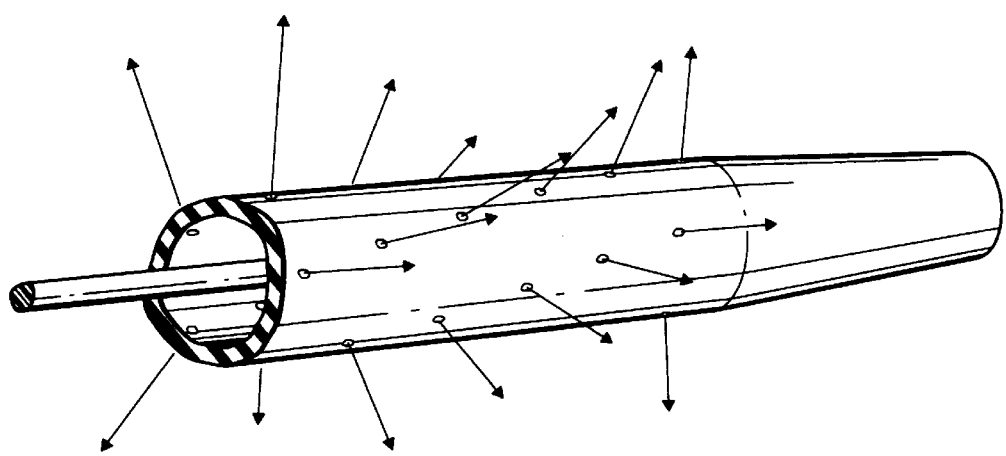
FIG. 4 is a perspective view of a portion of the spray pattern emitted by a preferred infusion catheter of the present invention.

FIG. 4 depicts the actual spray pattern made possible by the hole arrangement of the preferred infusion catheter depicted in FIGS. 2–4. Because of the double spiral configuration resulting from the distribution of holes as described above, the individual lines of spray are more completely dispersed compared to the prior art wherein the holes are aligned at strict 90° intervals.

Figure 5:
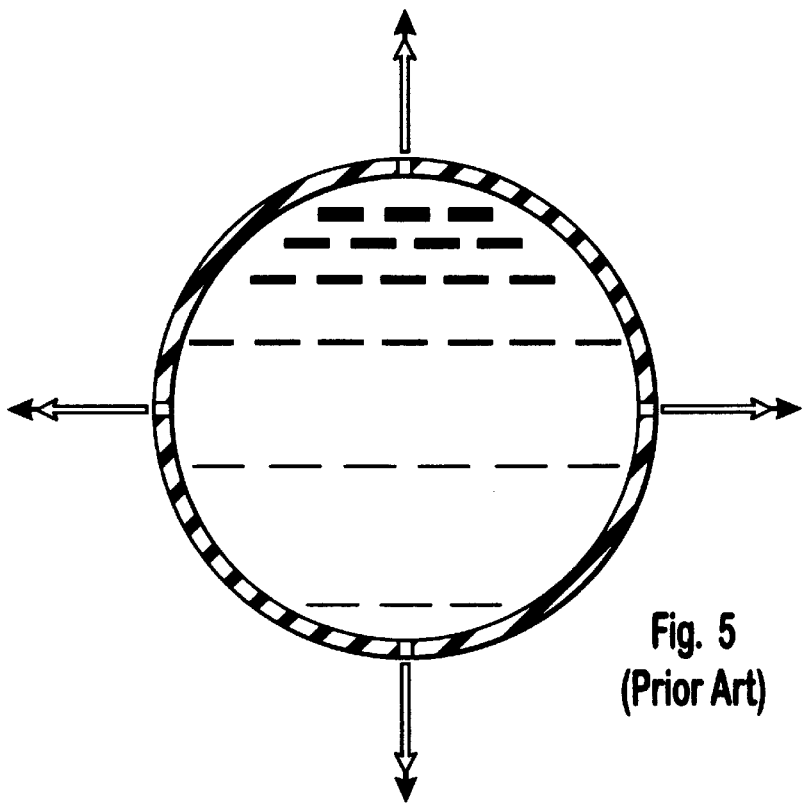
FIG. 5 is a transverse cross-section view of a prior art infusion catheter showing the spray pattern emitting therefrom.
Figure 6:
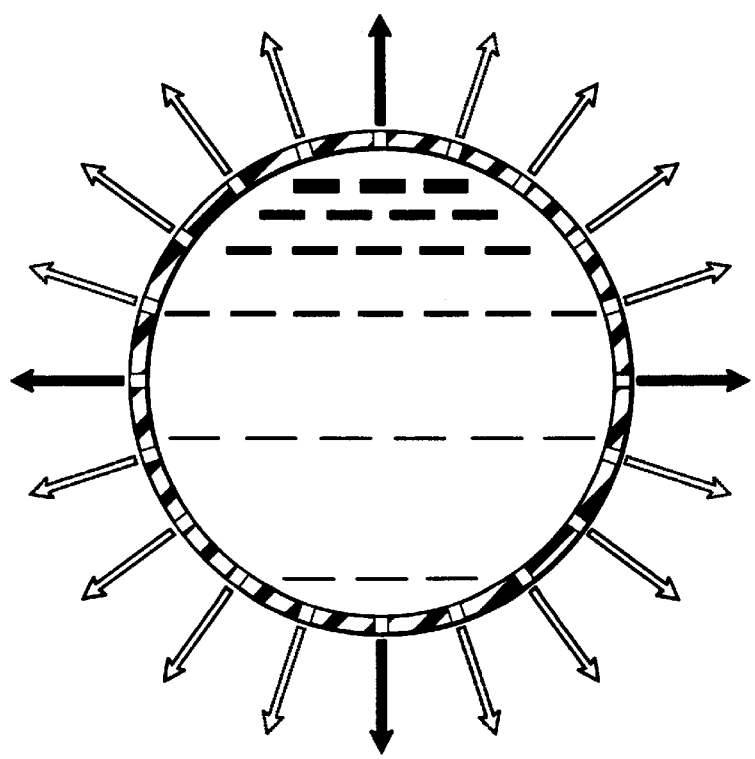
FIG. 6 is a transverse cross-section view of a preferred infusion catheter according to the present invention showing the spray pattern emitting therefrom.

FIGS. 5 and 6 show the difference in radial spray pattern between infusion catheters according to the prior art (FIG. 5) and the preferred infusion catheter of the present invention (FIG. 6). The differently shaded arrows represent successive radial cycles, or groups of four holes, along the length of the catheter. In prior art catheters, each successive cycle lines up along one of only four angular positions (0°, 90°, 180° and 270°) such that fluid is only infused through the catheter at each of the four angular positions around the circumference of the catheter. In contrast, the spray pattern according to the present invention delivers fluid at much tighter intervals, preferably at about 18° intervals.

Whereas the infusion holes 34 can be spaced at substantially regular longitudinal intervals, such as 0.050", it may be desirable in some cases to space the holes apart at somewhat irregular intervals. Moreover, the interval length between the holes can vary between about 0.030" to about 0.400" in order to provide varying concentrations of holes along the infusion length 32 of the infusion catheter 28. Nevertheless, it is generally preferred that the spacing be regular and that the interval be about 0.050".

The diameter of the infusion holes 34 may vary depending on the infusion length 32, which in turn affects the preferred number of holes along the infusion length. Typically, hole size will vary between about 0.002" to about 0.006". For an infusion length of 5 cm, it has been found that an infusion hole diameter of about 0.005" is preferred. For a catheter having an infusion length of 10 cm, which will effectively double the number of holes assuming constant longitudinal spacing, the preferred hole diameter is about 0.004". For an infusion length of 20 cm, which will double the number of holes again, the preferred hole diameter is about 0.003". For a catheter having an infusion length of 30 cm the preferred hole diameter is about 0.002".

Reducing the hole diameter as the number of holes is increased helps to maintain a more consistent rate of delivery between catheters of varying infusion length. A hole gradient of incrementally increasing hole size along the infusion length could alternately be employed to create a more even distribution of fluid through the holes. As fluid pressure decreases longitudinally down the length of the catheter, slightly increasing the hole size can nevertheless allow for more consistent outflow of fluid from all the holes.

The foregoing hole diameters are dictated by fluid dynamics in order to maintain a desired level of pressure within the catheter in order to ensure a substantially even distribution of thrombolytic fluid through each of the infusion holes 34 along the infusion length 32. If the holes are too large, then too much fluid will tend to escape out of the more length 32. If the holes are too large, then too much fluid will tend to escape out of the more proximal holes, which lowers the downstream fluid pressure such that too little fluid will tend to pass through the more distal holes.

In general, a catheter having an infusion length of 5 cm will have 40 infusion holes. A catheter having an infusion length of 10 cm will generally have 80 infusion holes. For an infusion length of 20 cm there will generally be 160 holes. For an infusion length of 30 cm there will be 240 holes. Hence, for systems where infusion holes are spaced apart at 0.050" intervals, there will be approximately 40 holes for every 5 cm of infusion length. Infusion lengths of up to 50 cm could also be employed.

The preferred catheter diameter is 5 French, although catheters of varying diameter (such as 3 or 4 French catheters) are possible depending on the size of the blood vessel being treated. For a 5 French catheter, the preferred outer diameter is 0.068"±0.0015" while the inner diameter is preferably about 0.048"±0.0015".

The infusion holes are preferably drilled using an excimer laser, although any known hole drilling techniques known in the art may be adapted and employed to form the infusion holes 34.

Figure 7:
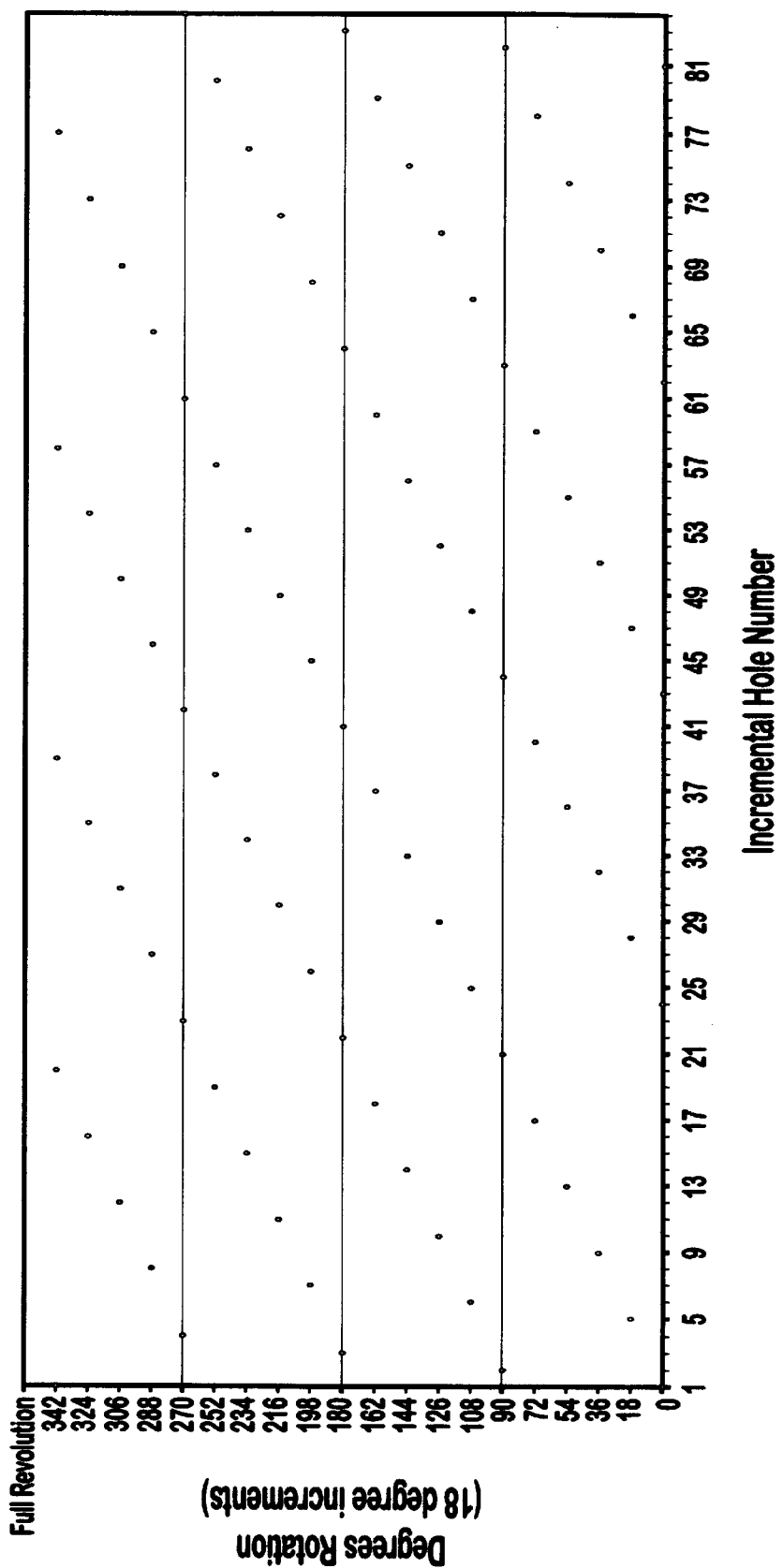
FIG. 7 is a chart showing the spacial relationship between the infusion holes within an infusion catheter according to one embodiment of the present invention.

In order to more precisely depict the preferred angular orientation of the infusion holes, reference is made to FIG. 7. FIG. 7 is a chart which shows the actual mathematical or spacial relationships between the infusion holes within a catheter according to a preferred embodiment of the present invention. In FIG. 7, each successive set of four holes is circumferentially offset relative to the immediately preceding set of four holes by 18°. Thus, it can be seen that the pattern repeats itself, or comes around to the starting point (0°), every sixth set. Thus, every five sets of four infusion holes, or every twenty holes, are angularly spaced apart such that no two holes are circumferentially aligned or arranged at the same angular orientation along the catheter. Thus, the outer wall of the infusion catheter 20 has a much more even distribution of holes thereabout in order to provide a more diverse spray pattern of thrombolytic fluids compared to prior art catheters.

Figure 8:
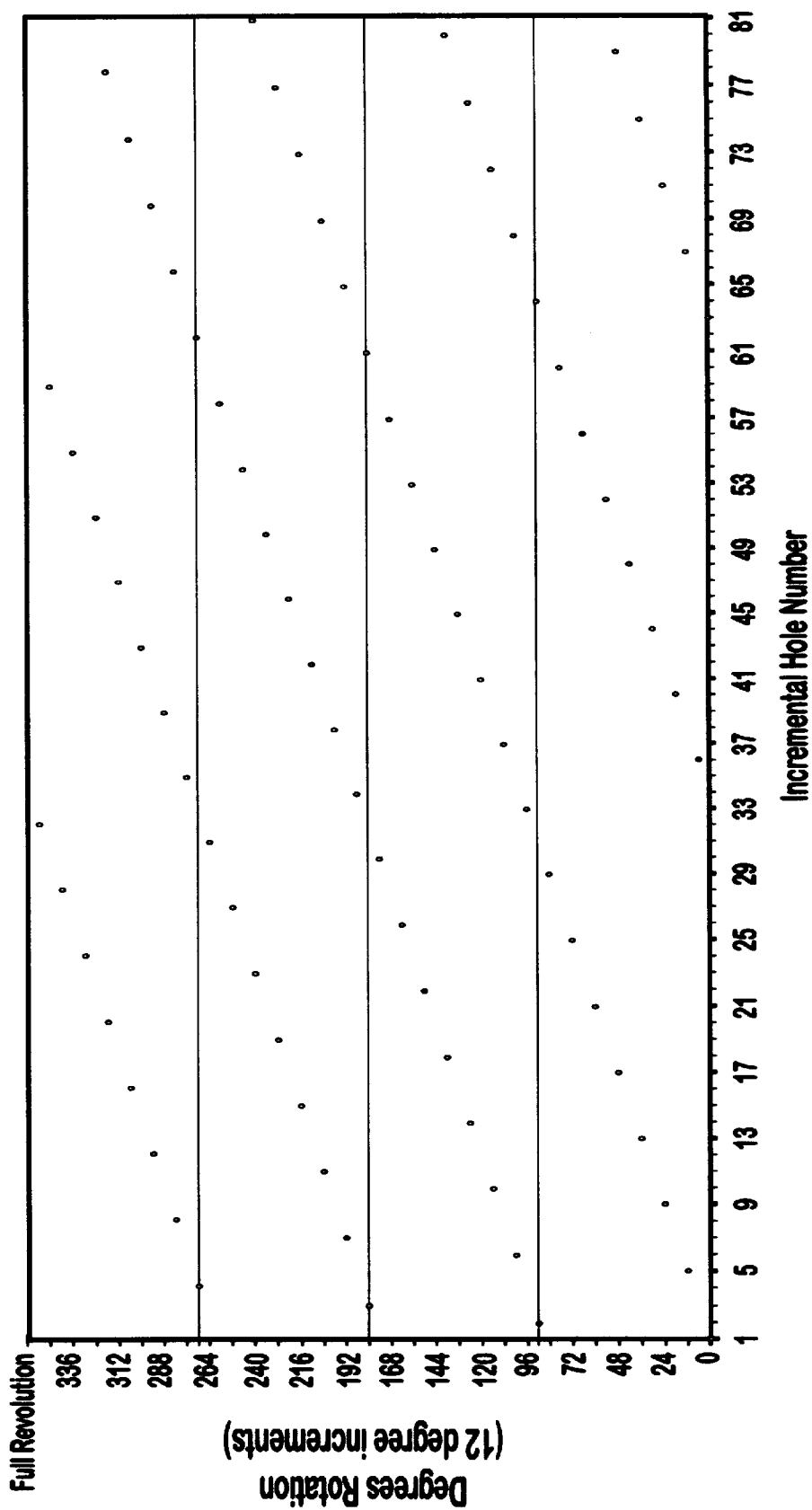
FIG. 8 is a chart showing the spacial relationship between the infusion holes in an alternative embodiment of the present invention.

FIG. 8 depicts the angular orientation of the infusion holes in an alternative embodiment of the present invention. In FIG. 8, each successive set of four holes is circumferentially offset from the preceding set of four holes by 12°. Since 12° does not evenly divide into 90°, but instead 180°, the hole placement does not repeat itself until after sixteen sets of holes, or 64 infusion holes, have been exhausted. The result is a tighter spray pattern compared to the spray pattern of the catheter mathematically depicted in FIG. 4.

Nevertheless, it is within the scope of the present invention to provide sets of holes that are circumferentially spaced or offset by any amount between 1° and 89°, although an angular distance of 18° is preferred. The result is varying amounts of angular offset that result in widely varying spray patterns. Any angular offset away from holes rigidly aligned along 90° intervals, as in the prior art, would be an improvement over the prior art and provide an improved spray pattern. Hence, sets of holes could also be angularly offset from immediately preceding sets by any amount between 91–179°, 181–269°, and 271–359°. The only limitation is that the angular offset provide a more diverse spray patter than where all the holes are spaced apart at regular 90° intervals.

Moreover, it is certainly within the scope of the invention to include more or less than 4 holes within the sets of holes discussed above. For instance, one may wish to design a spray pattern in which, e.g., three holes are circumferentially spaced apart by a radial distance of 90°, with the next set of three holes being offset by, e.g., 10° such that the second hole is radially spaced from the first by 90°, the third from the second by 90°, the fourth from the third by 100°, the fifth from the fourth by 90°, and so on. The important thing is that such arrangements yield a more diverse spray pattern than where all the holes are spaced apart at 90° intervals.

Although it may be preferred for the holes to be arranged in sets of four holes, with each successive hole being circumferentially spaced from an immediately preceding hole by 90°, other arrangements are possible. Although the holes within a given set may be separated by a variety of different angles θ, it will be preferable that the number and spacing of the holes within a given set be such that they will complete a cycle of about 360° before beginning the next set of holes. Thus, if the set includes n holes, then the radial spacing between successive holes in a given set will preferably be 360°/n. Thus, in the preferred embodiment, wherein each set of holes includes 4 holes, the radial spacing will be 90° between successive holes within the set.

Moreover, although the angle of offset between successive sets of holes is most preferably 18°, any angle that yields a reasonably diverse spay pattern can be used. However, the offset angle δ will preferably divide evenly into 360°, more preferably δ will divide evenly into 180°, and most preferably 6 will divide evenly into 90°. Note that 18° divides evenly into 90°. Selecting δ so that it divides evenly into, 360°, 180° or 90°, respectively, ensures some regularity of the hole pattern such that it is not overly random.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A catheter for introducing a liquid into the vascular system comprising:
    an elongated tubular body having a single lumen therethrough and an infusion length near a distal end thereof; and
    a plurality of infusion holes comprised of a plurality of sets of holes that are uniformly offset from one another both longitudinally and radially along the infusion length, each of which sets has at least three or more holes, each of said three or more holes being longitudinally spaced from one another and which together are radially spaced about the entire circumference of the catheter, and each set of holes being radially offset from an adjacent set of holes by a first radial angle, and each individual hole of each hole set being uniformly spaced from an adjacent hole in that hole set by a second angle.

2. A catheter as defined in claim 1, wherein said second angle is defined by θ=360°/n, wherein n is an integer greater than 1.

3. A catheter as defined in claim 2, wherein n is equivalent to the number of holes within each set of holes.

4. A catheter as defined in claim 3, wherein n=4 such that θ=90° and each set of holes includes 4 infusion holes.

5. A catheter as defined in claim 1, wherein first a radial angle is defined by δ which is an angle in a range selected from the group consisting of 1–89°, 91–179°, 81–269° and 271–359°.

6. A catheter as defined in claim 5, wherein δ divides evenly into 360°.

7. A catheter as defined in claim 6, wherein δ divides evenly into 90°.

8. A catheter as defined in claim 7, wherein δ equals 18°.

9. A catheter as defined in claim 1, wherein the infusion holes are longitudinally spaced at regular intervals of about 0.05 inch.

10. A catheter as defined in claim 1, wherein the infusion holes have a diameter in a range from about 0.002 inch to about 0.006 inch.

11. A catheter as defined in claim 1, wherein the infusion holes have a size gradient such that in an infusion length having a first hole and a last hole the last hole has a diameter greater than the diameter of the first hole.

12. A catheter as defined in claim 1, wherein the infusion length includes from between about 40 to about 240 holes.

13. A catheter with an improved spray pattern for introducing a liquid into the vascular system comprising:
    an elongated tubular body having a single lumen therethrough and an infusion length near a distal end thereof; and
    a plurality of infusion holes disposed along the infusion length of the tubular body, said infusion holes being comprised of a plurality of sets of holes that are uniformly offset from one another both longitudinally and radially along the infusion length, each of which sets has at least three or more holes, each of said three or more holes being longitudinally spaced from one another and which together are radially spaced about the entire circumference of the catheter, and each set of boles being radially offset from an adjacent set of holes by a first radial angle, and each individual hole of each hole set being uniformly spaced from an adjacent hole in that hole set by a second angle which is greater than the first angle.

14. A catheter as defined in claim 13, wherein each set of holes is comprised of n holes wherein n equals an integer greater than 1, and wherein said second angle is defined by an angular distance of about 360°/n, and wherein said first angle is defined by an angular distance of about x° such that the first hole of an immediately succeeding set is circumferentially offset from the nth hole of an immediately preceding set by an angle of about 360°/n+x°.

15. A catheter as defined in claim 13, wherein n=4 and x=18.

16. A catheter as defined in claim 13, wherein n=5 and x=15.

17. A catheter with an improved spray pattern for delivering a thrombolytic fluid medicament into the vascular system so that the fluid medicament is evenly delivered to a desired region in order to lyse a thrombus formed in the vascular system, said catheter comprising:

an elongated tubular body having a lumen therethrough through which the fluid medicament is delivered, said lumen comprising, an infusion length near a distal end thereof; and a plurality of infusion holes disposed along the infusion length of the tubular body, said infusion holes being comprised of a plurality of sets of holes that are uniformly offset from one another both longitudinally and radially alone the infusion length, each of which sets has at least three or more holes, each of said three or more holes being longitudinally uniformly spaced from one another and which together are uniformly radially spaced about the entire circumference of the catheter, and each set of holes being radially offset from an adjacent set of holes by a uniform first radial angle, and each individual hole of each hole set being spaced from at adjacent hole in that hole set by a second angle which is greater than the first angle.

18. A catheter as defined in claim 17, wherein each said set of holes comprises four holes and wherein said second angle is an angular distance of about 90°, and wherein said first angle is defined by an angular distance of x° such that the first hole of an immediately succeeding set is circumferentially offset from the fourth hole of an immediately preceding set by an angle of about 90°+x, wherein x° divides evenly into 90°.

19. A catheter as defined in claim 17, wherein x° is equal to 18° and wherein the infusion boles are longitudinally spaced at regular intervals of about 0.05 inch.

20. A catheter as defined in claim 17, wherein the infusion holes have a diameter in a range from about 0.002 inch to about 0.006 inch.

* * * * *

UNITED STATES PATENT AND TRADEMARK OFFICE
CERTIFICATE OF CORRECTION

PATENT NO. : 5,957,901

DATED : September 28, 1999

INVENTOR(S) : Jim Mottola, Steve W. Carlstrom, Andy E. Poursaid

It is certified that error appears in the above-identified patent and that said Letters Patent is hereby corrected as shown below:

Col. 4, ln. 32: after "evenly into" change "18 " to --180 --

Col. 4, ln. 62: after "that these" change "drawing" to --drawings--

Col. 6, ln. 24: after "18°" and before "relative" delete [,]

Col. 6, ln. 40: after "four" change "hole" to --holes--

Col. 9, ln. 10: after "spray" change "patter" to --pattern--

Col. 9, ln. 40: after "diverse" change "spay" to --spray--

Col. 9, ln. 43: after "preferably" change "6" to -- δ --

Col. 9, ln. 51: after "only as" change "illustrated" to --illustrative--

Col. 11, ln. 12: after "radially" change "alone" to --along--

Col. 12, ln. 1: after "from" change "at" to --an--

Col, 12, ln. 12: after "infusion " change "boles" to --holes--

Signed and Sealed this

Twenty-sixth Day of September, 2000

Attest:

Q. TODD DICKINSON

*Attesting Officer*          *Director of Patents and Trademarks*